United States Patent
Shimane et al.

(10) Patent No.: US 8,075,840 B2
(45) Date of Patent: Dec. 13, 2011

(54) AUTOMATIC MULTI-PURPOSE ANALYZER

(75) Inventors: Takanori Shimane, Hitachinaka (JP); Katsuaki Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 240 days.

(21) Appl. No.: 12/200,459

(22) Filed: Aug. 28, 2008

(65) Prior Publication Data

US 2009/0060785 A1    Mar. 5, 2009

(30) Foreign Application Priority Data

Aug. 31, 2007 (JP) .................... 2007-224998

(51) Int. Cl.
*G01N 21/00* (2006.01)

(52) U.S. Cl. ............... 422/63; 442/64; 442/65; 442/66; 442/67; 422/500; 422/501; 73/1.74

(58) Field of Classification Search ............. 422/63–67, 422/99–100, 500–501; 73/304, 1.74
See application file for complete search history.

(56) References Cited

U.S. PATENT DOCUMENTS 4,736,638 A    4/1988  Okawa et al.
6,107,810 A *  8/2000  Ishizawa et al. ............. 324/662

FOREIGN PATENT DOCUMENTS

| EP | 1 562 027 A1 | 8/2005 |
| JP | 3-189586 A | 8/1991 |
| JP | 2988362 | 10/1999 |
| JP | 2988362 B2 | 10/1999 |
| JP | 2006-010363 | 1/2006 |

* cited by examiner

*Primary Examiner* — Jyoti Nagpaul
(74) *Attorney, Agent, or Firm* — Mattingly & Malur, P.C.

(57) ABSTRACT

An automatic multi-purpose analyzer performs qualitative and quantitative analysis of biological samples such as blood, urine, etc. and includes a plurality of analysis units connected in series through a transfer line for transferring the sample, wherein failure caused by incorrect surface detection is resolved. The plurality of analysis units are connected in series through a transfer line for transferring a sample, each analysis unit including a pipetting mechanism for pipetting the sample, and wherein each of the analysis units includes a transmission mechanism for transmitting information about the amount of sample, obtained upon sample pipetting by the pipetting mechanism of each analysis unit, to other analysis units.

2 Claims, 6 Drawing Sheets

AUTOMATIC MULTI-PURPOSE ANALYZER

INCORPORATED BY REFERENCE

The present application claims priority from Japanese application 2007-224998 filed on Aug. 31, 2007, the contents of which are hereby incorporated by reference into this application.

BACKGROUND OF THE INVENTION

1. Field of the Invention

The present invention relates to an automatic multi-purpose analyzer which performs qualitative and quantitative analysis of biological samples such as blood, urine, etc. More particularly, the present invention relates to an automatic multi-purpose analyzer having a function for transferring a sample between a plurality of analysis units through a transfer apparatus.

2. Description of the Related Art

With the excellent measurement reproducibility, quantitative characteristics, and rapid analysis capabilities, a remarkably increasing number of automatic analyzers are used mainly in inspection centers and large hospitals. In particular, inspection centers which collect samples from local minor hospitals and analyze the samples on behalf of these hospitals are demanding a high-throughput analyzer capable of analyzing a number of samples in a short time. In order to meet this demand, a modularized analyzer having a plurality of analysis units connected in series through a transfer line is commercially available. Such a modularized analyzer is described, for example, in Japanese Patent No. 2988362.

SUMMARY OF THE INVENTION

An object of the present invention is to provide an automatic modularized multi-purpose analyzer that attains higher throughput.

In order to attain the above-mentioned object, the present invention is configured as follows:

An automatic multi-purpose analyzer having a plurality of analysis units connected in series through a transfer line for transferring sample liquid, each of the analysis units including a pipetting mechanism for pipetting sample liquid, wherein each of the analysis units includes a transmission mechanism for transmitting information about the amount of a sample liquid to other analysis units, the information being obtained upon sample pipetting by the pipetting mechanism of each of the analysis units An example will be explained below.

A mechanism used for first detecting the liquid surface to recognize its height (hereinafter referred to as surface height or surface level interchangeably) securely measures the surface height. Such a mechanism is based on a reliable liquid surface method. Information on the surface height is transferred to another analysis unit in which a capacitive sample probe is inserted into and then lowered inside a vessel. With the capacitive probe, capacitance fluctuation from a certain timing is monitored and, when the liquid surface is judged, lowering operation of the probe is stopped. This timing is referred to as reset time. With a conventional analyzer, it is not possible to know the height of the vessel at which the liquid surface resides and therefore monitoring is constantly required while the probe is lowered toward the vessel.

Therefore, when the tip of the sample probe almost reaches the entrance of the vessel, a reset signal is generated and a zero point of capacitance is set there. The capacitance gradually increases as the probe is inserted into and then lowered inside a deep sample vessel. When the probe comes in contact with the liquid surface, a hump signal fluctuation is obtained. When the analyzer captures the hump signal fluctuation, it recognizes the liquid surface. However, such a hump signal fluctuation also occurs owing to discharge noise or vibration generated while the probe is lowered and thereby incorrect surface detection will be made. With the present invention, the information on the place where the surface height is present can be obtained before the probe is lowered and therefore the reset signal is generated after the probe has approached the vicinity of the liquid surface (3 millimeters above the liquid surface). This makes it possible to ignore a hump signal occurring owing to discharge noise or vibration generated during lowering operation.

The liquid surface can be correctly detected if discharge noise during lowering operation can be ignored.

Fortunately, with a large-sized modularized automatic analyzer, a unit for measuring electrolyte in a sample is disposed, in many cases, on an upstream side of the transfer line for transferring the sample (because electrolyte measurement has urgency, that is, measurements should be obtained as soon as possible). Since a reaction vessel (dilution mixture vessel) into which the sample is discharged is a large-sized type, an electrolyte sample probe may be an electric probe, which can be easily inserted into the vessel. Therefore, it is the sample probe of an electrolyte analysis unit that is first inserted into the sample vessel. This sample probe correctly measures the surface height and transfers information on the height to another analysis unit for colorimetric measurement.

Sharing between analysis units information about the sample and liquid surface in the sample vessel obtained in the inspection operation makes it possible to omit surface detection to be performed by subsequent analysis units, thus improving the analysis efficiency. Further, even when liquid surface detection (hereinafter referred to simply as surface detection) is not omitted, if surface height information obtained by an analysis unit differs from surface height information obtained by the subsequent analysis unit, it can be determined that incorrect surface detection has been made because of, for example, air bubbles produced on the liquid surface of the sample. Thus, more reliable analysis can be attained.

DESCRIPTION OF THE PREFERRED EMBODIMENTS

An automatic multi-purpose analyzer pipettes sample liquid such as blood, urine, etc. and reagent liquid into a reaction vessel and analyzes the mixture thereof. In recent years, a capacitive liquid level detection method has been used widely for liquid level detection because the outer diameter of its sample probe can be reduced. The reason the outer diameter reduction is necessary is that a reaction vessel has been remarkably reduced in size to about 2 mm×4 mm because of reduced amounts of reaction liquid. Accordingly, a capacitive probe having an outer diameter of 1 millimeter or less is suitable for use as a sample probe that is inserted into such a small reaction vessel. Although an electric probe is most reliable because it is free from misdetection, this type of probe requires two electrodes, which increases the outer diameter to 4 millimeters; thus, the probe may not fit into a reaction vessel. Thus, the capacitive liquid level detection method has been used widely. With the capacitive liquid level detection method, discharge noises may occur depending on the charged state in the sample vessel, resulting in liquid level misdetection by a sample pipetting mechanism.

A present modularized automatic multi-purpose analyzer commonly includes detection means for detecting a liquid surface level for each pipetting mechanism. In a sample pipetting mechanism of a modular analysis unit, even if a liquid surface level is misdetected due to discharge noises, that modular analysis unit alone cannot determine whether or not misdetection has occurred. In the automatic multi-purpose analyzer having multiple modular analysis units according to the present invention, a modular analysis unit shares with other modular analysis units liquid surface level information (amount of sample liquid) obtained by the analysis unit, which allows any of the analysis units to verify liquid surface level information obtained from the pipetting devises of other analysis units. This allows the automatic multi-purpose analyzer to avoid incorrect analysis caused by incorrect liquid surface level information.

An embodiment of the present invention will be described below with reference to the accompanying drawings.

Figure 1:
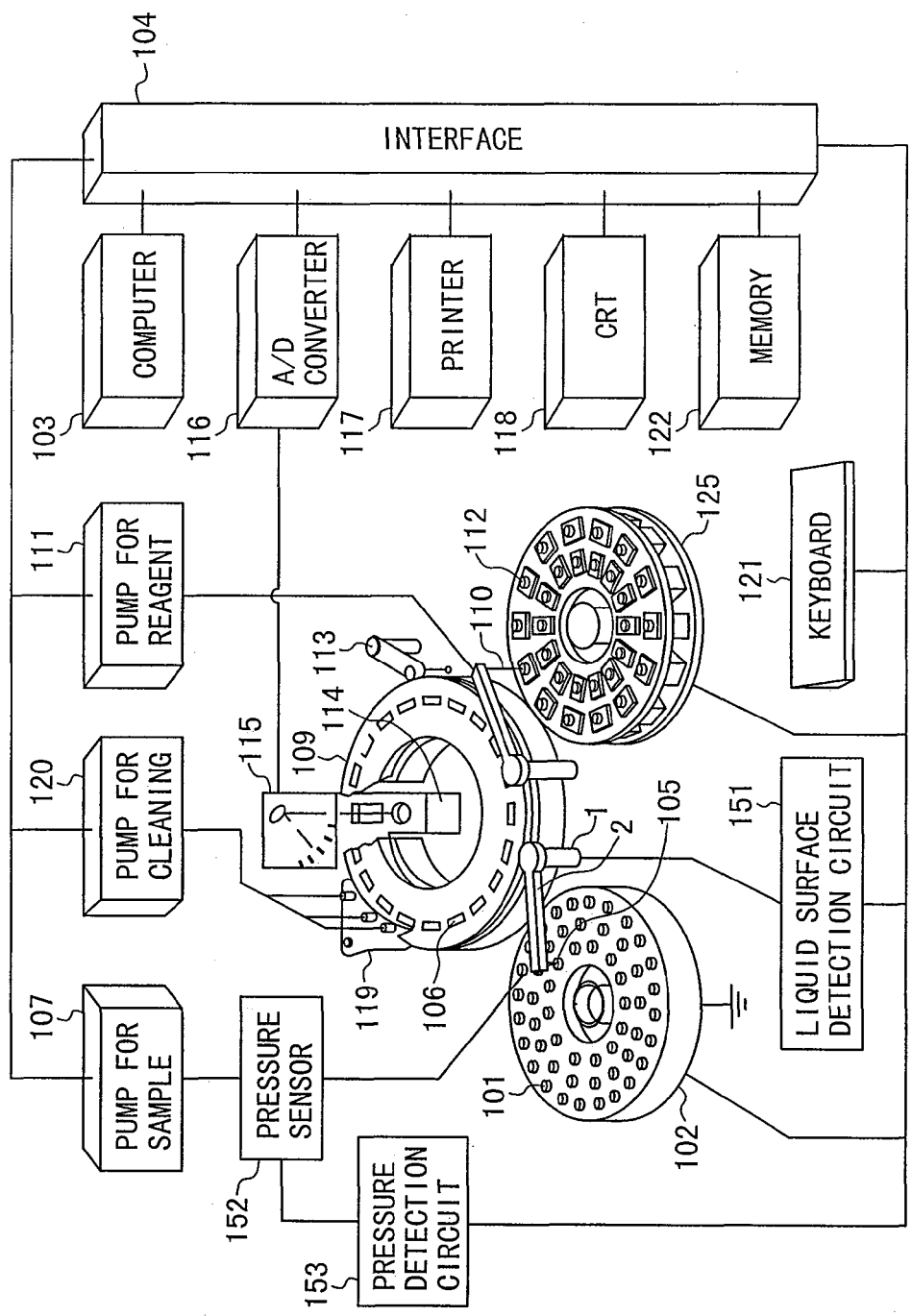
FIG. 1 is a schematic diagram showing the overall configuration of an analysis unit according to the present invention.

FIG. 1 is a schematic diagram of the periphery of pipetting mechanisms of a common automatic analyzer. Since the functions of respective sections are well-known, detailed description of the functions will be omitted. The automatic multi-purpose analyzer is configured such that a sample pipetting arm 2 of a sample pipetting mechanism 1 moves vertically and rotates, and a sample pipetting probe 105 attached to the sample pipetting arm 2 suctions a sample liquid 7 in a sample vessel 101 installed on a horizontally-rotating sample disk 102 and discharges the sample liquid 7 into a reaction vessel 106. As shown in FIG. 1, the sample disk 102 is typically universally designed to accommodate sample vessels; that is, a sample vessel 101 can be placed directly on the sample disk 102, or the sample vessel 101 can be placed on a test tube (not shown) installed on the sample disk 102.

The configuration of the automatic multi-purpose analyzer of FIG. 1 will be explained below in more detail. A rotatable reagent disk 125 installs thereon reagent bottles 112, each being associated with a plurality of analysis items subjected to analysis. A reagent pipetting probe 110 attached to a movable arm pipettes a predetermined amount of reagent liquid from a reagent bottle 112 to a reaction vessel 106.

The sample pipetting probe 105 performs sample suction and discharge operations in response to the operation of a sample syringe pump 107. The reagent pipetting probe 110 performs reagent suction and discharge operations in response to the operation of a reagent syringe pump 111. Analysis items to be analyzed for each sample are input from input devices such as a keyboard 121 or the screen of a CRT 118. The operation of each unit in the automatic multi-purpose analyzer is controlled by a computer 103.

With the intermittent rotation of the sample disk 102, a sample vessel 101 is transferred to a sample suction position, and the sample pipetting probe 105 is lowered into the sample vessel 101 in a halted state. When the tip of the sample pipetting probe 105 comes in contact with the surface of the sample liquid with the lowering operation of the sample pipetting probe 105, a liquid surface level detector 151 outputs a detection signal, and the computer 103 performs control so as to stop the lowering operation by the drive unit of the movable sample pipetting arm 2 based on the detection signal. Then, the sample pipetting probe 105 suctions a predetermined amount of the sample liquid and rises to the upper dead center. While the sample pipetting probe 105 is suctioning a predetermined amount of the sample liquid, a pressure detection circuit 153 monitors pressure fluctuation inside a passage between the sample pipetting probe 105 and the sample syringe pump 107 by use of a signal from a pressure sensor 152. If an abnormal pressure fluctuation is detected during the suction operation, that means the predetermined amount of the sample liquid may not have been suctioned, and an alarm is therefore added to related analysis data.

Then, the sample pipetting arm 2 horizontally swings to lower the sample pipetting probe 105 at the position of a reaction vessel 106 on a reaction disk 109, and the sample pipetting probe 105 discharges the sample liquid into the reaction vessel 106. When the reaction vessel 106 containing the sample is moved to a reagent addition position, a reagent liquid associated with a relevant analysis item is added from the reagent pipetting probe 110 into the reaction vessel 106. During the sample and reagent pipetting operations, the liquid surface levels of the sample liquid in the sample vessel 101 and of the reagent liquid in the reagent bottle 112 are detected. The mixture of the sample and reagent in the reaction vessel is stirred by a stirring device 113. The reaction vessel containing the mixture is then transferred to measurement means. At the same time, an actuator opens shielding means of a light source 114, and the luminescence value or absorbance of the mixture is measured by a photo-multiplier 115 or photometer as the measurement means. The resultant luminescence signal passes through an A/D converter 116 and then is supplied to the computer 103 through an interface 104 to calculate concentrations for analysis items. Analysis results are printed out by a printer 117 through the interface 104 or displayed on the screen of the CRT 118 and, at the same time, stored in a hard disk 122 or memory. The reaction vessel 106 that completed the photometry is cleaned at the position of a cleaning mechanism 119. A cleaning pump 120 supplies cleaning water to the reaction vessel while discharging waster water from the reaction vessel. In the example of FIG. 1, three concentric rows of vessel holding sections are formed on the sample disk 102 so as to concentrically set sample vessels 101 in three rows, and a sample suction position for the sample pipetting probe 105 is provided in each concentric row.

Figure 2:
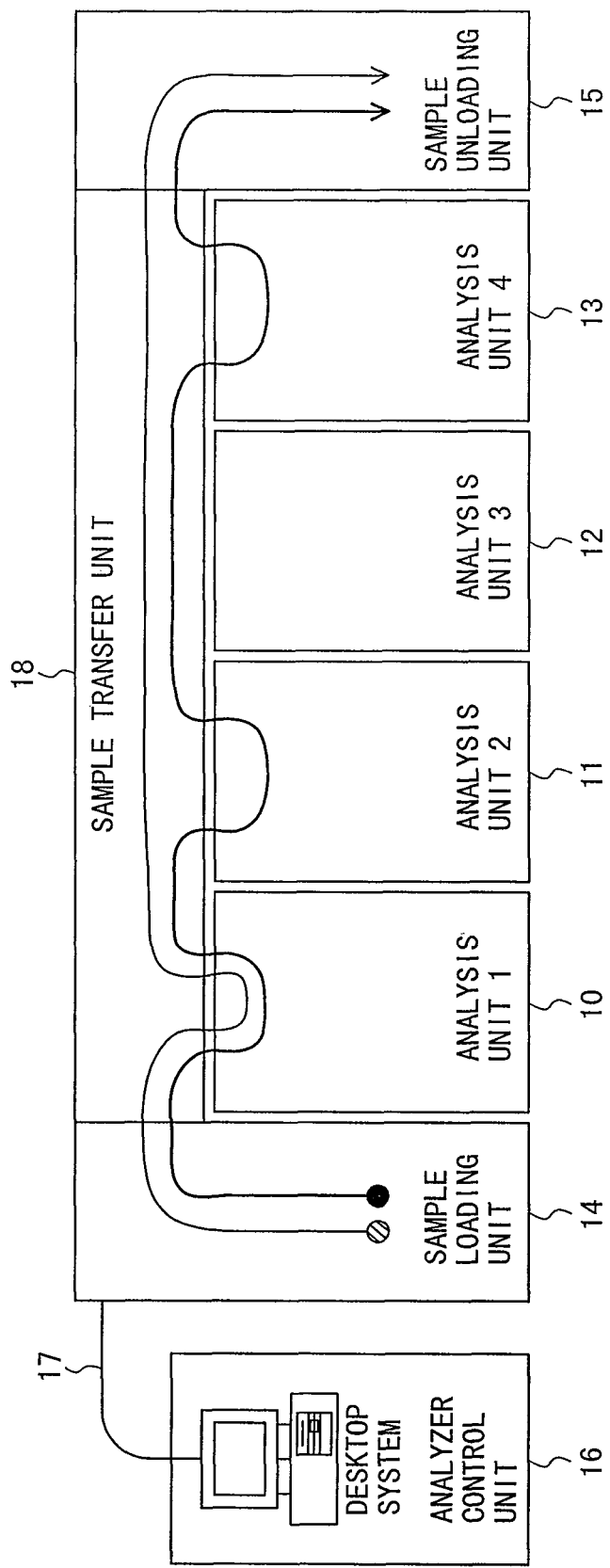
FIG. 2 is a schematic diagram showing the overall configuration of an automatic multi-purpose analyzer having a plurality of analysis units.

An example of an automatic multi-purpose analyzer configured with a plurality of analysis units connected in series will be explained below with reference to FIG. 2. The plurality of analysis units having the above-mentioned functions are connected in series by a sample transfer unit. An analyzer control unit serves as a user interface of the automatic multi-purpose analyzer, and interfaces inside the automatic multi-purpose analyzer are connected via suitable communication means such as Ethernet (registered trademark). A sample vessel is loaded from the sample loading unit and then transferred by the sample transfer unit to an analysis unit which is requested for analysis. The sample vessel that completed analysis is suitably transferred to the sample unloading unit. FIG. 2 shows a specific example of two different sample transfer paths: one is for a case where only an analysis unit 1 (10) is requested for analysis, and the other for a case where the analysis unit 1 (10), an analysis unit 2 (11), and an analysis unit 4 (13) are requested for analysis.

Figure 3:
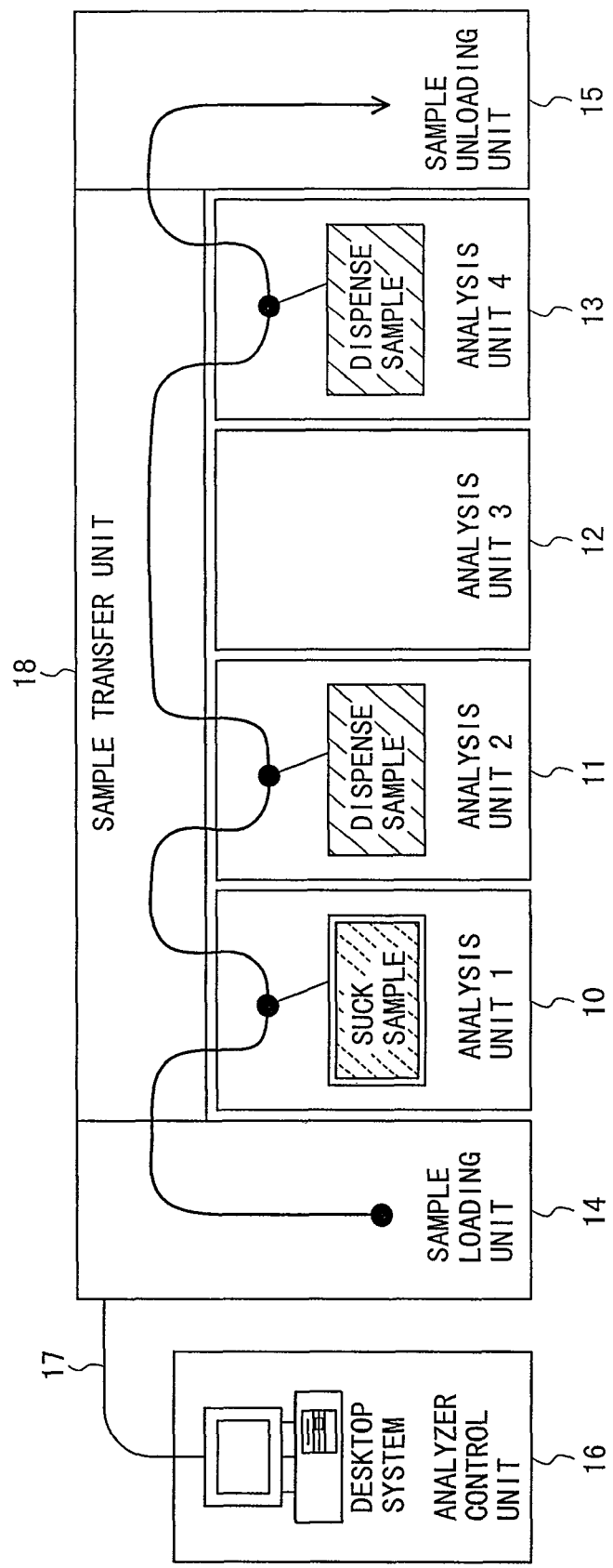
FIG. 3 shows a problem to be solved by the present invention.

Problems with present automatic multi-purpose analyzers will be explained below with reference to FIG. 3. Assume that the sample transfer unit is requested to transfer a sample vessel 101 to the analysis unit 1 (10), the analysis unit 2 (11), and the analysis unit 4 (13) for analysis, as stated above for FIG. 2. The sample vessel 101, requested by the analyzer control unit 16, is loaded from the sample loading unit 14 and then supplied to the analysis unit 1 (10) for analysis. As mentioned above, the sample pipetting probe 105 is lowered into the sample vessel 101, the lowering operation by the drive unit of the movable arm (sampling arm) 2 is stopped, and the pipetting probe 105 suctions a predetermined amount of sample. If the pipetting probe detects the liquid surface of the sample during the suction operation, the sample is transferred from the analysis unit 1 (10) to the analysis unit 2 (11) and then to the analysis unit 3 (12) so as to be subjected to pipetting operation by each individual analysis unit. Accordingly, even if the sample is normally detected by the analysis unit 1 (10), the sample is subjected to incorrect detection by the pipetting probe of the analysis unit 2 and then transferred to the sample unloading unit 15, resulting in degraded reliability of overall automatic analysis.

Figure 4:
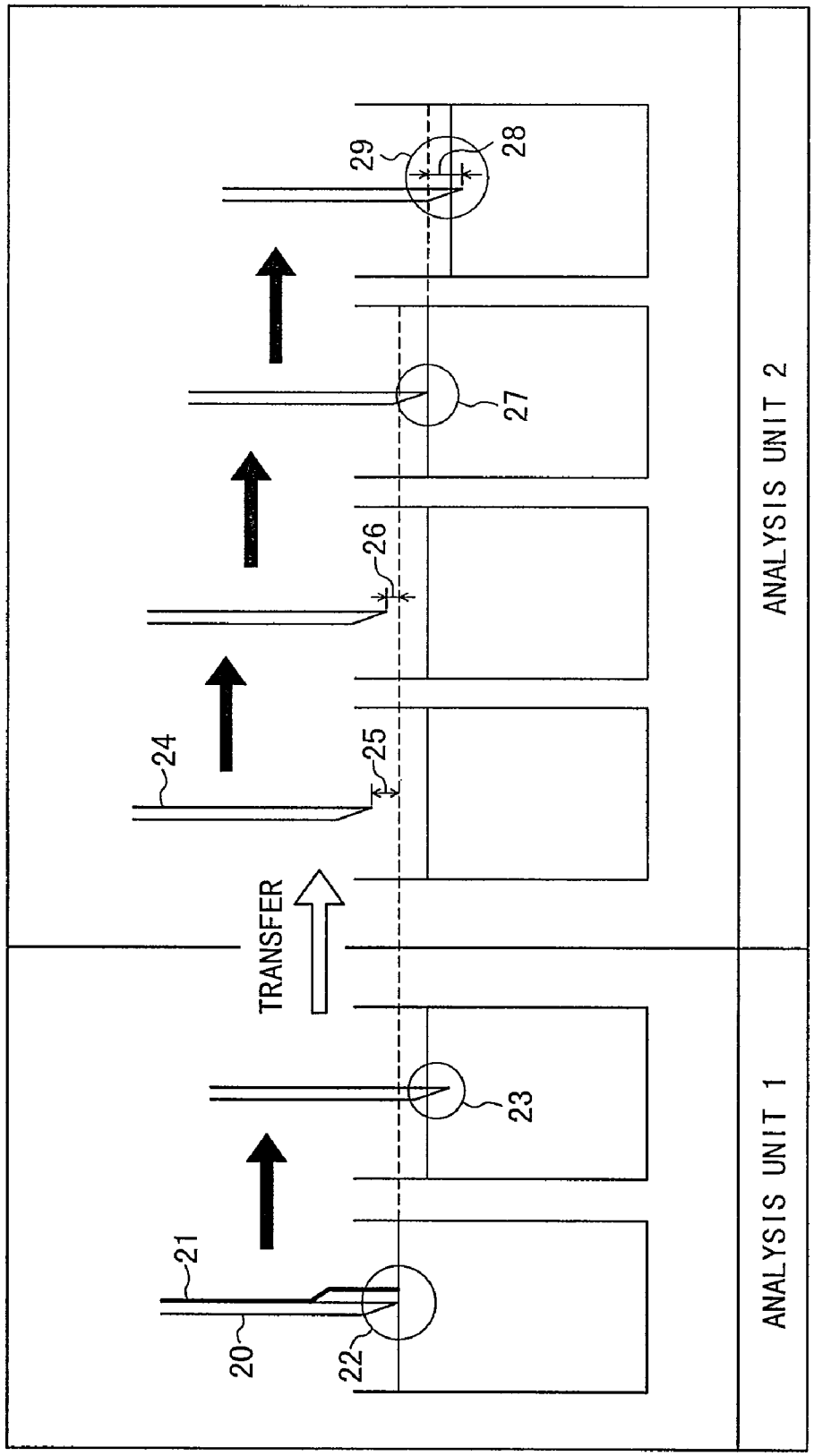
FIG. 4 is a schematic diagram of the automatic multi-purpose analyzer according to the present invention.

The operation of the automatic multi-purpose analyzer according to the present invention will be explained below with reference to FIGS. 3 and 4.

The analysis unit 1 (10) includes an electrolyte (Na+, K+, and Cl-ion) measurement apparatus. Since the sample probe 20 of the analysis unit 1 (10) is an electric probe 21, the sample probe 20 is highly reliable and therefore almost never fail. Further, a detection signal obtained is clear because of the ON/OFF (conducting/nonconducting) detection method.

A liquid surface level 22 can also be correctly recognized. Even if there is not a request on electrolyte, the probe is inserted to measure the liquid surface level 22 and then lowered to a suction position 23. The liquid surface level information is once transferred to the CPU of the apparatus control unit 16 controlling the entire automatic multi-purpose analyzer and then to the analysis unit 2 (11) therefrom. A pipetting probe 24 of the analysis unit 2 (11) is a capacitive probe having a small outer diameter, and therefore can be easily inserted into a reaction vessel.

Figure 5:
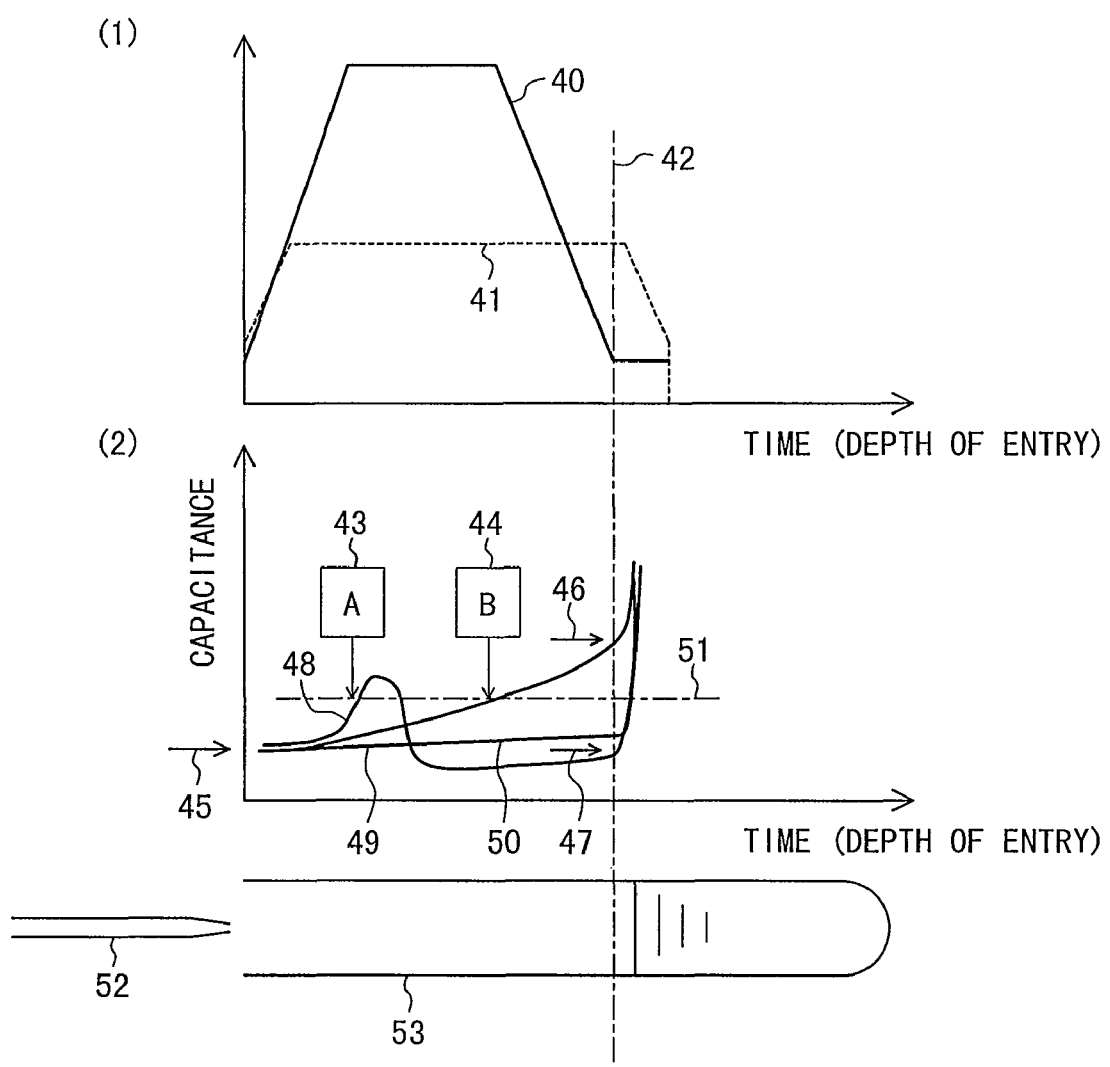
FIG. 5A is a graph showing a relation between the probe lowering speed and time, and FIG. 5B showing a relation between a surface detection signal output and time.

The liquid surface level information is transferred to the pipetting probe 24 of the analysis unit 2 (11). Based on the information, the pipetting probe 24 is lowered at high speed until it reaches a position 25, 5 millimeters above a surface position 22 of the analysis unit 1 during sample suction operation. Then, the lowering speed of the pipetting probe 24 is slowed down until it reaches a position 26, 2 millimeters above the surface position 22. The lowering operation is continued at a constant low speed and then a liquid surface 27 is detected. The pipetting probe 24 is stopped at a position 28, 1.5 millimeters below the liquid surface. FIG. 5(1) is a graph showing a relation between the probe lowering speed and time, and FIG. 5(2) showing a relation between a surface detection signal output and time. With a conventional automatic multi-purpose analyzer, immediately before lowering operation starts (45), a reset signal is generated when the tip of the probe is in the vicinity of the entrance of the sample vessel, and the output voltage at this timing is set as a zero point. In FIG. 5(1), a detection speed curve 41 of the conventional automatic multi-purpose analyzer indicates that the probe moves at a constant speed until it reaches the liquid surface while a speed curve 40 of the automatic multi-purpose analyzer according to the present invention indicates that the probe moves at high speed. With a detection signal pulse curve of FIG. 5(2), the probe is lowered into the sample vessel while observing a detection signal. When the detection signal reaches and exceeds a fixed value (threshold value 51), it is judged that the probe has come in contact with the liquid surface. However, depending on the charging state in the sample vessel (in particular, a plastic blood collection pipe is easy to be charged and, after a centrifuge or the like is used for serum separation, the blood collection pipe is charged very intensively), the capacitance of a charge-time pulse signal 49 gradually increases as the probe is lowered, and exceeds the threshold value 51 although the probe has not yet come in contact with the liquid surface. In this case, a portion B (44) is incorrectly detected. If discharge takes place between the sample vessel inner surface and the probe, a hump waveform is generated in a pulse signal 48 at a portion A (43) during probe lowering operation. Also if the hump signal exceeds the threshold value 51, incorrect surface detection results. Since a pulse signal 50 according to the present invention transmits the liquid surface level with a certain accuracy, a reset trigger signal of the surface detection signal is generated 2 millimeters above the liquid surface (42). With the charge-time pulse signal 49, an arrow portion 46 is reacknowledged as a zero point; with the discharge-time pulse signal 48, an arrow portion 47 is reacknowledged as a zero point.

The probe 52 is vertically moved by a stepping motor. Therefore, it is necessary to lower the probe 52 while counting the number of pulses given to the motor and, when the number of pulses reaches a certain number, generate a reset trigger signal, and lowers the probe 52 into a sample vessel 53.

Since capacitance fluctuations from the reacknowledged zero points are monitored, the signal increases only slightly by charge, and discharge does not take place, during a short time (and in a short distance) since the probe is 2 millimeters above the liquid surface until it comes in contact with the liquid surface, remarkably increasing the reliability of surface detection.

Using the zero point as a reference position of the pipetting start position of the analysis unit 2 (11), the probe detects the liquid surface 27 from the reference position, and surface information having correction for lowered liquid surface by sample suction 29 is transmitted to an analysis unit 4 (13). The analysis unit 4 (13) performs the same pipetting probe control as that performed by other analysis units. This makes it possible to reduce incorrect surface detection operations by the pipetting probe of each analysis unit to shorten the processing time, thus contributing to provision of an optimal operating environment for the automatic multi-purpose analyzer.

Although the first analysis unit installs therein an electrolyte measurement unit, it is also possible to dispose a mechanism dedicated for surface detection for securely measuring the liquid surface level between the sample loading unit 14 and the first analysis unit, and transmit the surface information to each analysis unit.

Figure 6:
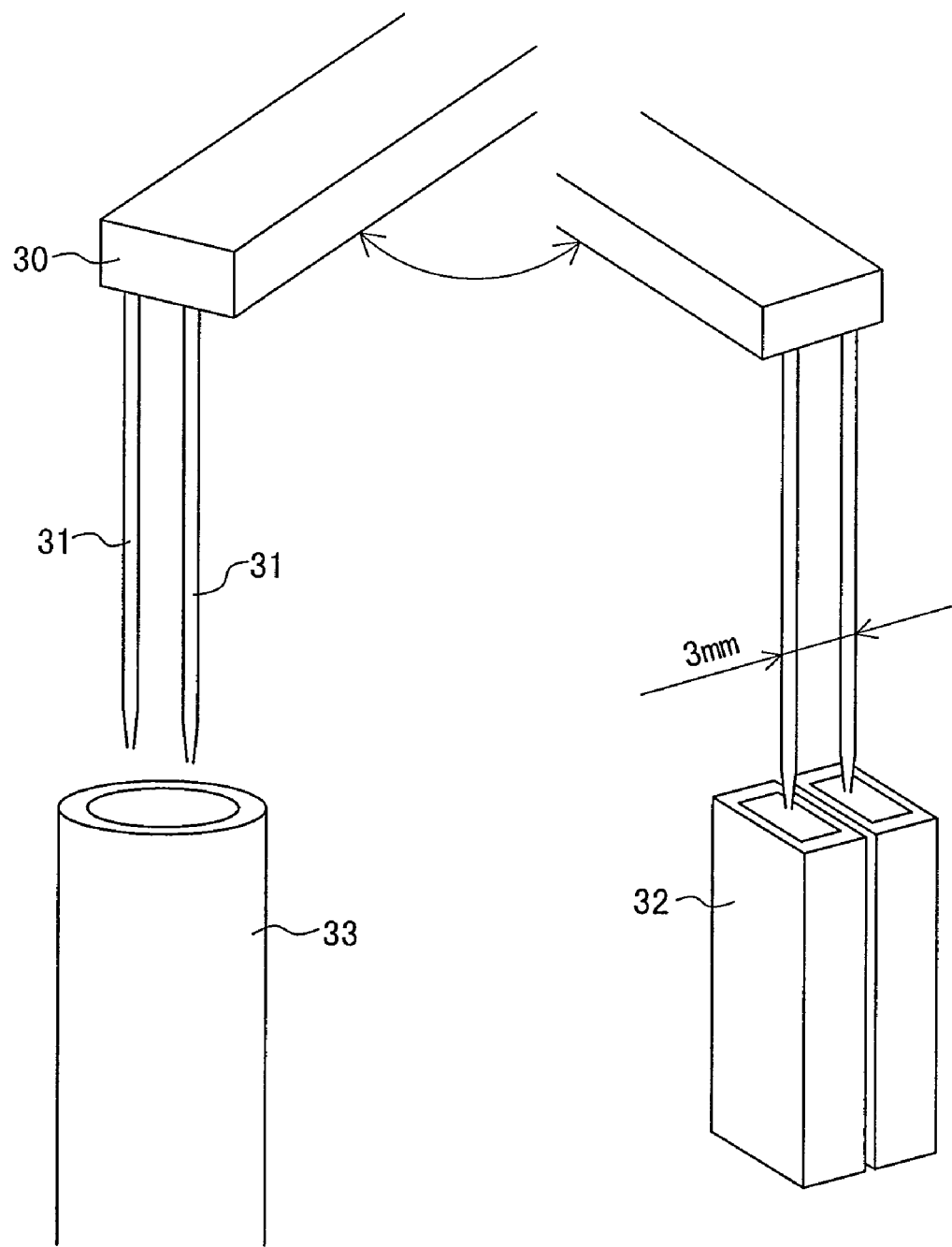
FIG. 6 is a schematic diagram of an electric surface detection apparatus.

A configuration for surface detection as shown in FIG. 6 is also possible. In the first analysis unit, an arm 30 is provided with two sample probes 31 in parallel with each other, and conduction between the two probes is monitored. Recently, reaction vessels 32 are placed at very small intervals, that is, about 3 millimeters; however, it is easy to insert the probes into a sample vessel 33 (having an inner diameter of 8 millimeters) with the original gap between nozzles.

As means for first inserting the probe into the vessel to measure the liquid surface, it is also possible to lower the probe while discharging air from the tip of the nozzle and detect pressure fluctuation inside the nozzle at the moment when the probe comes in contact with the liquid surface.

There is another advantage if the liquid surface is preliminarily known. If the liquid surface is approximately known, the sample probe can be lowered at high speed and slowed down in the vicinity of the liquid surface and accordingly the pipetting time can be shortened, thus improving the analysis throughput of the automatic multi-purpose analyzer.

What is claimed is:

1. An automatic multi-purpose analyzer having a plurality of analysis units connected in series through a transfer line for transferring a sample liquid, each of the analysis units including a pipetting mechanism for pipetting sample liquid and for providing a liquid surface level detecting mechanism, wherein:

each of the analysis units includes a transmission mechanism configured to transmit information about a height of a liquid surface level of a sample vessel obtained by the liquid surface level detecting mechanism to other analysis units, the information being obtained upon sample pipetting by the pipetting mechanism of each of the analysis units;

a liquid surface level detecting mechanism provided in a pipetting mechanism of another analyzer for which the information about the height of the liquid surface level is transmitted by the transmission mechanism is controlled, wherein:

the liquid surface level detecting mechanism which transmits the information is an electric liquid surface level detecting mechanism, and the liquid surface level detecting mechanism to which the information is transmitted and controls the liquid surface level detecting mechanism is a capacitive liquid surface level detecting mechanism; and the liquid surface level detecting mechanism, to which the information is transmitted and controls the liquid surface level detecting mechanism, is configured to recognize a zero level which is a higher predetermined level than the height of the liquid surface level obtained by the liquid surface level detecting mechanism which transmits the information, and is configured to detect the liquid surface level based on a capacitance at the zero level.

2. An automatic multi-purpose analyzer having a plurality of analysis units connected in series through a transfer line for transferring sample liquid, each of the analysis units including a pipetting mechanism for pipetting sample liquid and for providing a liquid surface level detecting mechanism, wherein:

each of the analysis units includes a transmission mechanism configured to transmit information about a height of a liquid surface level of a sample vessel obtained by the liquid surface level detecting mechanism to other analysis units, the information being obtained upon sample pipetting by the pipetting mechanism of each of the analysis units; and a control unit configured to verify whether information of the height of the liquid surface level obtained by the liquid surface level detecting mechanism provided in the pipetting mechanism of another analyzer is correct.

* * * * *